United States Patent
Johansson et al.

(10) Patent No.: US 10,449,098 B2
(45) Date of Patent: Oct. 22, 2019

(54) WEARABLE DISPOSABLE ABSORBENT ARTICLE

(71) Applicant: ESSITY HYGIENE AND HEALTH AKTIEBOLAG, Göteborg (SE)

(72) Inventors: Marie Johansson, Göteborg (SE); Hans Een, Göteborg (SE); Joanna Campillo, Göteborg (SE)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 16/099,319

(22) PCT Filed: May 10, 2016

(86) PCT No.: PCT/EP2016/060405
§ 371 (c)(1),
(2) Date: Nov. 6, 2018

(87) PCT Pub. No.: WO2017/194093
PCT Pub. Date: Nov. 16, 2017

(65) Prior Publication Data
US 2019/0133845 A1    May 9, 2019

(51) Int. Cl.
*A61F 13/514* (2006.01)
*A61F 13/49* (2006.01)
(Continued)

(52) U.S. Cl.
CPC .. *A61F 13/51478* (2013.01); *A61F 13/51484* (2013.01); *A61F 13/51496* (2013.01);
(Continued)

(58) Field of Classification Search
CPC ............ A61F 13/49012; A61F 13/4906; A61F 13/49063; A61F 13/49413; A61F 13/4942;
(Continued)

(56) References Cited

U.S. PATENT DOCUMENTS 7,754,044 B2 *  7/2010  Wada ................. A61F 13/15593
                                                           156/250
8,840,600 B2 *  9/2014  Takeuchi .......... A61F 13/49011
                                                            604/385.24
(Continued)

FOREIGN PATENT DOCUMENTS

EP         2862549 B1      8/2017
WO      WO-97/31603 A1   9/1997
(Continued)

OTHER PUBLICATIONS

Decision to Grant dated May 20, 2019 issued in Russian patent application No. 2018143389 (11 pages) and its English-language translation thereof (8 pages).

*Primary Examiner* — Catharine L Anderson
(74) *Attorney, Agent, or Firm* — Drinker Biddle & Reath LLP

(57) ABSTRACT

A wearable disposable absorbent article includes a front panel, a back panel, and a crotch panel bridging and at least partially overlapping the front and back panels. A backsheet of the crotch panel has a laminate structure including a liquid barrier sheet and a nonwoven layer arranged on top of each other. The liquid barrier sheet extends over the entire length of the crotch panel and further over at least a portion of each of the front and back panels. The nonwoven layer extends at least over the entire length of the crotch panel but not over a length of more than 40 mm over each of the front and back panels. The width of the nonwoven layer is smaller than the width of the liquid barrier sheet.

16 Claims, 3 Drawing Sheets

(51) Int. Cl.
    *A61F 13/15*     (2006.01)
    *A61F 13/51*     (2006.01)

(52) U.S. Cl.
    CPC ............... *A61F 13/49061* (2013.01); *A61F 2013/15869* (2013.01); *A61F 2013/15878* (2013.01); *A61F 2013/51026* (2013.01); *A61F 2013/51452* (2013.01)

(58) Field of Classification Search
    CPC ............ A61F 13/51478; A61F 13/5148; A61F 13/51484; A61F 13/51496; A61F 2013/49076
    See application file for complete search history.

(56) References Cited

U.S. PATENT DOCUMENTS

| | | |
|---|---|---|
| 2008/0132871 A1 | 6/2008 | Otsubo |
| 2009/0240221 A1 | 9/2009 | Rothenberger et al. |
| 2011/0208152 A1 | 8/2011 | Trennepohl et al. |
| 2013/0324957 A1 | 12/2013 | Gassner et al. |
| 2016/0058628 A1 | 3/2016 | Morimoto et al. |

FOREIGN PATENT DOCUMENTS

| | | |
|---|---|---|
| WO | WO-2011/106360 A2 | 9/2011 |
| WO | WO-2012/014660 A1 | 2/2012 |
| WO | WO-2013/161700 A1 | 10/2013 |
| WO | WO-2013/167179 A1 | 11/2013 |

\* cited by examiner

A - A

B - B

WEARABLE DISPOSABLE ABSORBENT ARTICLE

CROSS-REFERENCE TO PRIOR APPLICATION

This application is a § 371 National Stage Application of PCT International Application No. PCT/EP2016/060405 filed May 10, 2016, which is incorporated herein in its entirety.

TECHNICAL FIELD

The present disclosure relates to a wearable disposable absorbent article, such as a diaper, an incontinence garment or a feminine garment, including a front panel, a back panel, and a crotch panel bridging the front panel and the back panel.

TECHNICAL BACKGROUND

Wearable disposable absorbent articles, such as diapers, incontinence garments, feminine garments and the like, have wide-spread utility in both domestic and institutional settings for such purposes as the care of infants, the management of bodily efflux or exudate and the management of incontinence.

Known wearable disposable absorbent articles comprise a front panel, a back panel, and a crotch panel bridging the front panel and the back panel. The crotch panel comprises a topsheet, a backsheet, and an absorbent core provided between the topsheet and the backsheet. Absorbent articles of this type are disclosed in WO 2012/014660 A1, WO 2013/161700 A1, US 2008/0132871 A1 and US 2009/0240221 A1.

In the absorbent article of WO 2012/014660 A1, the backsheet of the crotch panel has an outer nonwoven cloth which extends along the entire length of the crotch panel.

Such a nonwoven cloth gives the outer surface of the absorbent article a comfortable, cloth-like feel. However, the nonwoven cloth may obscure printed regions provided on the front panel and/or the back panel and/or restrict the areas of these panels in which printing can be performed without subsequent obstruction by the cloth. Further, cutting out portions of the nonwoven cloth, so as to provide printable areas, results in significant material losses, thus increasing the production costs.

Hence, there remains a need for a wearable disposable absorbent article which is soft and pliable, yields a large printable area, allowing for clear and sharp prints with good visibility to be provided, and can be manufactured in a cost-efficient manner, while offering a high degree of leakage protection.

SUMMARY

Accordingly, it is desired to provide a wearable disposable absorbent article which is soft and pliable, yields a large printable area, allowing for clear and sharp prints with good visibility to be provided, and can be manufactured in a cost-efficient manner, while offering a high degree of leakage protection. This can be achieved by a wearable disposable absorbent article with the technical features given in the following.

The wearable disposable absorbent article, such as a wearable disposable absorbent hygiene article, comprises a front panel, a back panel, and a crotch panel bridging and at least partially overlapping the front panel and the back panel. In an embodiment, the crotch panel comprises a topsheet, a backsheet, and an absorbent core provided between the topsheet and the backsheet. The backsheet has a laminate structure comprising a liquid barrier sheet and a nonwoven layer arranged on top of each other, wherein the nonwoven layer is arranged at an outer side of the crotch panel, facing away from a wearer of the absorbent article when worn. The liquid barrier sheet extends over the entire length, in the direction from the front panel towards the back panel, of the portion of the crotch panel arranged between the front panel and the back panel, and the liquid barrier sheet further extends over at least a portion of the front panel and over at least a portion of the back panel. The nonwoven layer extends at least over the entire length, in the direction from the front panel towards the back panel, of the portion of the crotch panel arranged between the front panel and the back panel. The nonwoven layer does not extend over the front panel over a length, in the direction from the front panel towards the back panel, of more than 40 mm. Further, the nonwoven layer does not extend over the back panel over a length, in the direction from the front panel towards the back panel, of more than 40 mm. The width, in the direction perpendicular to the direction from the front panel towards the back panel, of the nonwoven layer is smaller than the width, in the direction perpendicular to the direction from the front panel towards the back panel, of the liquid barrier sheet.

Herein, any shapes, sizes, dimensions, relative dimensions etc. given for the absorbent article relate to the fully unfolded and laid out flat state of the absorbent article. In this regard, any elastic forces possibly acting on the absorbent article, e.g., due to the presence of elastic elements such as elastic waist cuffs or leg cuffs, are ignored. For the definitions of the shapes, sizes, dimensions, relative dimensions etc. given for the absorbent article herein, the absorbent article is treated as if no such elastic forces were present.

Herein, any shapes, sizes, dimensions, relative dimensions etc. given for the different components of the absorbent article relate to the fully unfolded and laid out flat states of these components. In this regard, any elastic forces possibly acting on the different components of the absorbent article, e.g., due to the presence of elastic elements such as elastic waist cuffs or leg cuffs, are ignored. For the definitions of the shapes, sizes, dimensions, relative dimensions etc. given for the different components of the absorbent article herein, the components are treated as if no such elastic forces were present.

Herein, the term "nonwoven" defines a material made of fibers or filaments, such as a fabric, which is neither woven nor knitted.

The backsheet herein is a structure comprising a nonwoven layer and a liquid barrier sheet, wherein the backsheet is arranged to face away from the wearer of the absorbent article when worn and adapted to prevent liquid from passing through.

The nonwoven layer arranged at the outer side of the crotch panel can give the outer surface of the absorbent article a comfortable, cloth-like feel.

The nonwoven layer has no overlap with the front panel and the back panel or only has a small overlap with the front panel and/or the back panel of not more than 40 mm. Hence, large printable areas are present on the front and back panels, which allows for clear and sharp prints with good visibility. Further, cutting out portions of the nonwoven material in order to provide these printable areas is not necessary, so that material losses can be kept to a minimum. In this way, the production costs are minimised.

The nonwoven layer may have an overlap with the front panel and/or the back panel of not more than 40 mm, or not more than 30 mm, or not more than 20 mm. By providing such a small overlap or such small overlaps, production margins or tolerances are compensated, so that it can be particularly reliably ensured that the entire length, in the direction from the front panel towards the back panel, of the portion of the crotch panel arranged between the front panel and the back panel is provided with the nonwoven layer. In this way, the desired outer texture of this portion of the crotch panel can be achieved with high production efficiency.

The nonwoven layer may extend over the front panel over a length, in the direction from the front panel towards the back panel, in the range of 5 mm to 40 mm, or 10 mm to 30 mm. The nonwoven layer may extend over the back panel over a length, in the direction from the front panel towards the back panel, in the range of 5 mm to 40 mm, or 10 mm to 30 mm.

The nonwoven layer may not extend over the front panel. The nonwoven layer may not extend over the back panel.

The nonwoven layer may extend only over the entire length, in the direction from the front panel towards the back panel, of the portion of the crotch panel arranged between the front panel and the back panel.

The width, in the direction perpendicular to the direction from the front panel towards the back panel, of the nonwoven layer is smaller than the width, in the direction perpendicular to the direction from the front panel towards the back panel, of the liquid barrier sheet. By providing a smaller amount of nonwoven material in the width direction in this manner, a particularly soft and pliable absorbent article with a high degree of leakage protection is obtained.

The nonwoven layer may be made of thermoplastic polymer material fibers or filaments. The nonwoven layer may be formed by a variety of different processes, such as spunbonding, airlaying, meltblowing or bonded carded web formation processes. In particular, the nonwoven layer may be made of an SMS (spunbond/meltblown/spunbond) or SS (spunbond/spunbond) nonwoven material of polypropylene or bicomponent fibers of polypropylene and polyethylene, or of a combination of such materials.

The nonwoven layer may have a basis weight in the range of 10 $g/m^2$ to 20 $g/m^2$.

The liquid barrier sheet may be made of a plastic material, for example a thermoplastic film material, and/or a nonwoven material. For example, the liquid barrier sheet may be formed as a plastic layer, e.g., a thermoplastic layer, or a plastic film, e.g., a thermoplastic film. Forming the liquid barrier sheet of a plastic material, in particular, a thermoplastic film material, allows for a particularly good printability of the liquid barrier sheet.

The liquid barrier sheet may be a liquid impermeable, breathable or non-breathable layer. The liquid barrier sheet may consist of a single layer or have a laminate structure with a plurality of layers, e.g., two or more layers, three or more layers, or four or more layers. The layers of the liquid barrier sheet may be laminated, bonded or attached to each other, for example, by thermo-mechanical bonding, such as thermosealing, ultrasonic bonding, such as ultrasonic welding, an adhesive or adhesives, stitching or the like.

In particular, the liquid barrier sheet may be a breathable microporous film. The microporous film may be made of a material comprising at least two basic components, namely a thermoplastic elastomeric polyolefin polymer and a filler.

These components and, in some embodiments, additional other components can be mixed together, heated and subsequently extruded into a mono-layer or multi-layer film using any one of various film-producing processes, such as cast embossed, chill and flat cast, and blown film processes.

On a dry weight basis, based on the total weight of the microporous film, the film may include from approximately 30 weight-% to approximately 60 weight-% of the thermoplastic elastomeric polyolefin polymer, or blend thereof, and from approximately 40 weight-% to approximately 70 weight-% of the filler. Other components, such as additives and/or ingredients, for example, antioxidants and/or stabilisers and/or pigments, may be included in the film.

The filler may consist of one or more materials selected from calcium carbonate ($CaCO_3$), various kinds of clay, silica ($SiO_2$), alumina, barium carbonate, sodium carbonate, magnesium carbonate, talc, barium sulfate, magnesium sulfate, aluminium sulfate, titanium dioxide ($TiO_2$), zeolites, cellulose-type powders, kaolin, mica, carbon, calcium oxide, magnesium oxide, aluminium hydroxide, pulp powder, wood powder, cellulose derivatives, chitin and chitin derivatives. A suitable coating, such as, for example, stearic acid, may be applied to the filler particles.

The liquid barrier sheet may have a basis weight in the range of 8 $g/m^2$ to 22 $g/m^2$, or 9 $g/m^2$ to 20 $g/m^2$, or 10 $g/m^2$ to 18 $g/m^2$.

The liquid barrier sheet may extend over the entire length, in the direction from the front panel towards the back panel, of the crotch panel. In this way, a large printable area on the liquid barrier sheet, allowing for clear and sharp prints with good visibility to be achieved, can be provided.

The topsheet of the crotch panel is arranged to face the wearer of the absorbent article when worn. The topsheet is a liquid permeable layer adapted to allow a liquid, such as urine or other bodily fluids, to pass through.

The topsheet may consist of a single layer or have a laminate structure comprising a plurality of layers, for example, two or more layers, three or more layers, or four or more layers. The layers may be made of the same material, or some or all of the layers may be made of different materials.

The layer of the topsheet or, for the case of a laminate structure, one, some or all of the layers of the topsheet may be made of a single material or have plural portions made of different materials, e.g., within different parts of the wearer-facing surface of the topsheet.

The layer of the topsheet or, for the case of a laminate structure, one, some or all of the layers of the topsheet may be a nonwoven material, a perforated plastic film, a plastic or textile mesh, or a liquid permeable foam layer.

The layer of the topsheet or, for the case of a laminate structure, one, some or all of the layers of the topsheet may be, for example, a hydrophilic, non-apertured nonwoven web of fibers, such as natural fibers, e.g., cotton or pulp fibers, synthetic fibers, e.g., polyester or polypropylene fibers, or a combination of these fibers.

The topsheet may have a basis weight in the range of 10 $g/m^2$ to 25 $g/m^2$.

The absorbent core is provided between the topsheet and the backsheet to absorb the liquid, such as urine or other bodily fluids, which has passed through the topsheet. The absorbent core may be made of any suitable absorbent or liquid uptake material, such as one or more layers of cellulose fluff pulp, foam, fiber waddings or the like.

The absorbent core may contain fibers or particles of absorbent polymer material, in particular, superabsorbent material. Superabsorbent materials have the ability to absorb and retain large quantities of liquid upon formation of a hydrogel. For example, the superabsorbent material may be surface cross-linked, partially neutralised polyacrylates.

The superabsorbent material, e.g., the superabsorbent fibers or particles, may be mixed with other absorbent or liquid uptake material or materials, such as cellulose fluff pulp, and/or arranged in pockets or layers in the absorbent core. The ratio of superabsorbent material and pulp in the absorbent core may be 0% to 80% pulp fibers and 100% to 20% superabsorbent material.

The absorbent core may further comprise components for improving the properties of the absorbent core. For example, the absorbent core may comprise a binder or binders, such as binder fibers, and/or a liquid-dispersing material or materials, and/or a liquid acquisition material or materials etc.

The wearable disposable absorbent article may comprise more than one absorbent core, e.g., two absorbent cores. For example, the absorbent article may comprise an upper absorbent core and a lower absorbent core, wherein the upper absorbent core is arranged closer to the wearer of the absorbent article when worn.

As has been detailed above, the crotch panel bridges and at least partially overlaps the front panel and the back panel. The crotch panel may extend over the front panel over a length, in the direction from the front panel towards the back panel, in the range of 80 mm to 200 mm, or 100 mm to 150 mm. The crotch panel may extend over the back panel over a length, in the direction from the front panel towards the back panel, in the range of 80 mm to 200 mm, or 100 mm to 150 mm.

The liquid barrier sheet may extend over the front panel over a length, in the direction from the front panel towards the back panel, in the range of 80 mm to 200 mm, or 100 mm to 150 mm. The liquid barrier sheet may extend over the back panel over a length, in the direction from the front panel towards the back panel, in the range of 80 mm to 200 mm, or 100 mm to 150 mm.

The nonwoven layer may be arranged relative to the liquid barrier sheet so that a center line of the nonwoven layer along the direction from the front panel towards the back panel is substantially congruent with a center line of the liquid barrier sheet along the direction from the front panel towards the back panel.

The nonwoven layer may be arranged relative to the liquid barrier sheet so that a center line of the nonwoven layer along the direction perpendicular to the direction from the front panel towards the back panel is substantially congruent with a center line of the liquid barrier sheet along the direction perpendicular to the direction from the front panel towards the back panel.

The length, in the direction from the front panel towards the back panel, of the nonwoven layer may be in the range of 40% to 70%, or 45% to 60%, of the length, in the direction from the front panel towards the back panel, of the liquid barrier sheet.

In particular embodiments, the width, in the direction perpendicular to the direction from the front panel towards the back panel, of the nonwoven layer is smaller than the width, in the direction perpendicular to the direction from the front panel towards the back panel, of the liquid barrier sheet by not more than 50 mm, or by 5 mm to 40 mm, or by 10 mm to 30 mm.

The crotch panel may further comprise a nonwoven cuff material, such as a standing gather, wherein inner edges of the nonwoven cuff material at the outer side of the crotch panel extend along the direction from the front panel towards the back panel. The inner edges of the nonwoven cuff material may be spaced apart from each other by a distance in the direction perpendicular to the direction from the front panel towards the back panel. The width, in the direction perpendicular to the direction from the front panel towards the back panel, of the nonwoven layer may be larger than the distance between the inner edges of the nonwoven cuff material, so that the nonwoven layer extends beyond each of the inner edges of the nonwoven cuff material in the direction perpendicular to the direction from the front panel towards the back panel. In this way, the outer surface of the crotch panel can be provided with a particularly comfortable structure.

For example, the nonwoven cuff material may consist of a single layer or have a laminate structure comprising a plurality of layers, e.g., two or more layers, three or more layers, or four or more layers. The layer of the nonwoven cuff material or, for the case of a laminate structure, one, some or all of the layers of the nonwoven cuff material is or are made of a nonwoven material. The nonwoven material may be a thermoplastic material, such as an SMS or SS nonwoven material of polypropylene or bicomponent fibers of polypropylene and polyethylene, or a combination of such materials.

The nonwoven cuff material may have a basis weight in the range of 10 $g/m^2$ to 20 $g/m^2$.

The nonwoven cuff material may consist of a single piece of material or of plural, in particular, two, separate pieces of material.

For example, the nonwoven cuff material may be a layer or layers, e.g., a nonwoven layer or nonwoven layers, which is or are wrapped around side edges of the remainder of the crotch panel, so that, at the outer side of the crotch panel, the nonwoven cuff material extends inward from each of the side edges towards a center line of the crotch panel, i.e., the center line extending along the direction from the front panel towards the back panel. In this case, the nonwoven cuff material extends from each of the side edges of the remainder of the crotch panel towards the center line along only a portion of the width of the remainder of the crotch panel, so that the inner edges of the nonwoven cuff material at the outer side of the crotch panel, which extend along the direction from the front panel towards the back panel, are spaced apart from each other by a distance in the direction perpendicular to the direction from the front panel towards the back panel.

In particular, the nonwoven cuff material may consist of two separate pieces of material, each of which is wrapped around a respective one of the side edges of the remainder of the crotch panel, so that, at the outer side of the crotch panel, the nonwoven cuff material extends inward from each of the side edges towards a center line of the crotch panel.

The nonwoven cuff material may be provided with elastic threads, such as elastic threads made of spandex. The elastic threads may be made of fibers, e.g., spandex fibers, with a titer in the range of 300 to 1100 dtex and an elongation of 100% to 300%.

The nonwoven layer may extend beyond each of the inner edges of the nonwoven cuff material in the direction perpendicular to the direction from the front panel towards the back panel by 30 mm or less, or by 1 mm to 25 mm, or by 5 mm to 20 mm.

The front panel and/or the back panel and/or the crotch panel may have a substantially rectangular shape in plan view. The nonwoven layer may have a substantially rectangular shape in plan view. The liquid barrier sheet may have a substantially rectangular shape in plan view.

Providing the front panel and/or the back panel and/or the crotch panel and/or the nonwoven layer and/or the liquid barrier sheet so as to have a substantially rectangular shape in plan view allows for the respective component or components to be manufactured in a particularly simple manner, substantially without any cutting losses. Therefore, the production efficiency can be increased, while at the same time minimising the production costs.

The wearable disposable absorbent article may have an H-shape in plan view. In particular, such a shape of the absorbent article can be obtained by choosing a front panel, a back panel and a crotch panel each having a substantially rectangular shape in plan view.

An absorbent article having such an H-shape in plan view can be manufactured in a particularly simple manner, substantially without any cutting losses.

Alternatively, the wearable disposable absorbent article may have, for example, an hourglass or a dog bone shape.

The liquid barrier sheet may have one or more printed areas at the portion thereof which overlaps with the front panel and/or the portion thereof which overlaps with the back panel. The nonwoven layer may not extend into the one or more printed areas. In this case, it can be ensured in a particularly reliable and efficient manner that clear and sharp prints with good visibility are provided.

The liquid barrier sheet and the nonwoven layer may be attached to each other by thermo-mechanical bonding, such as thermosealing, ultrasonic bonding, such as ultrasonic welding, an adhesive or adhesives, stitching or the like.

The wearable disposable absorbent article may be a diaper, in particular, a pull-on diaper or a pants-type diaper, an incontinence garment or a feminine garment.

The nonwoven layer may consist of a single piece of nonwoven material. In this case, the nonwoven layer can be manufactured in a particularly simple manner.

BRIEF DESCRIPTION OF THE DRAWINGS

For a better understanding of the present disclosure and to show how the same may be carried into effect, reference will now be made, by way of example only, to the accompanying drawings, in which.

DETAILED DESCRIPTION OF PARTICULAR EMBODIMENTS

A particular embodiment of the present disclosure will now be described with reference to the accompanying drawings.

Figure 1:
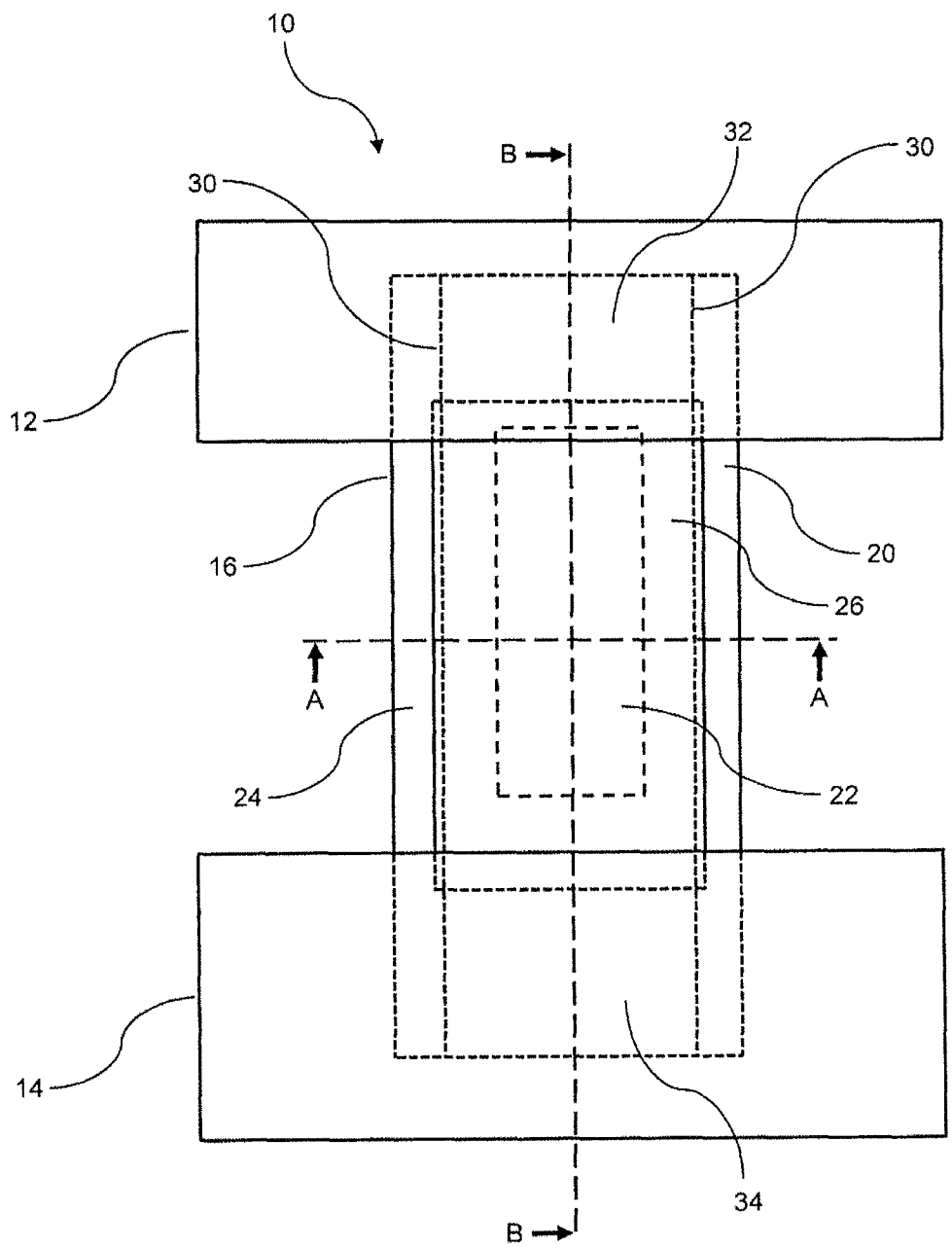
FIG. 1 shows a schematic bottom view of a wearable disposable absorbent article according to an embodiment of the present disclosure in an unfolded state thereof.

FIG. 1 shows a schematic bottom view of a wearable disposable absorbent article 10 according to an embodiment of the present disclosure. The wearable disposable absorbent article 10 is a diaper. In FIG. 1, the absorbent article 10 is shown in a fully unfolded and laid out flat state. As is shown in FIG. 1, the absorbent article 10 has an H-shape in plan view.

Figure 2:
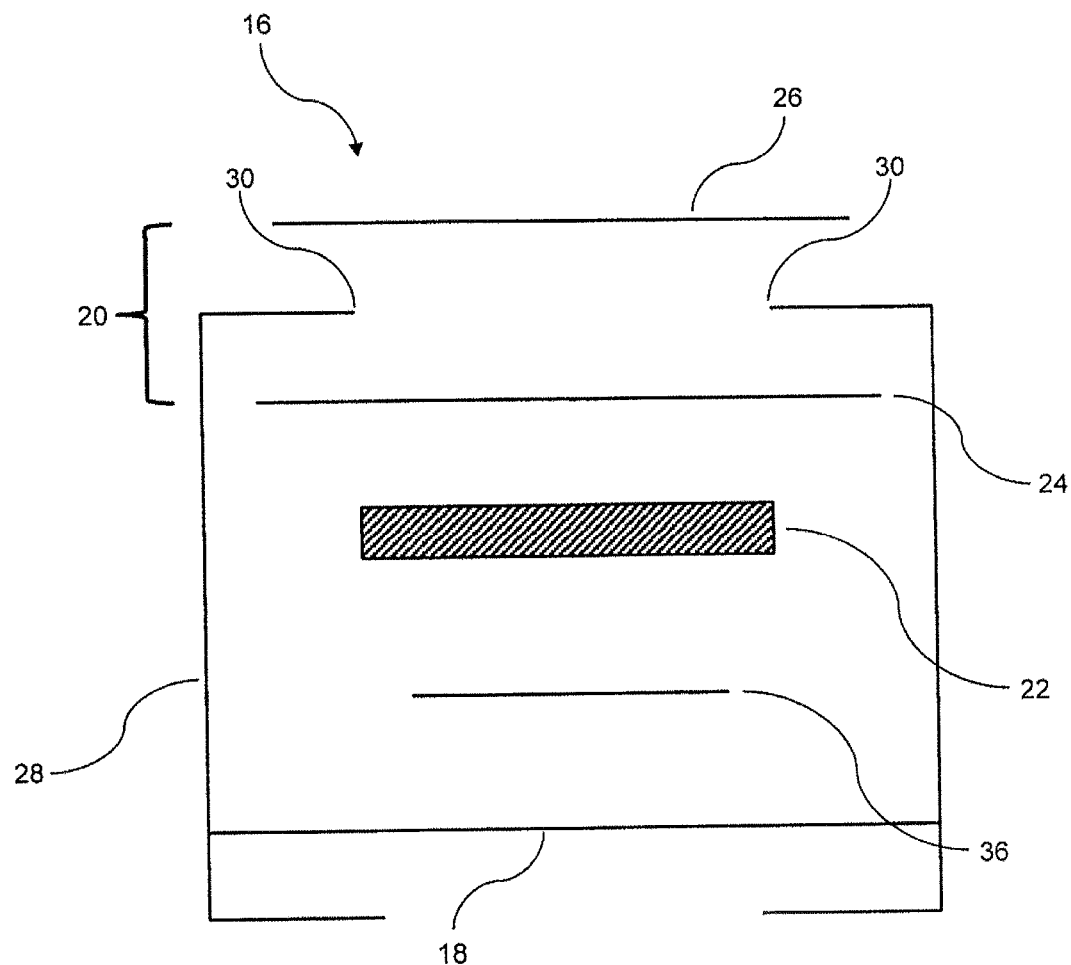
FIG. 2 shows a schematic exploded cross-sectional view taken along the line A-A in FIG. 1.
Figure 3:
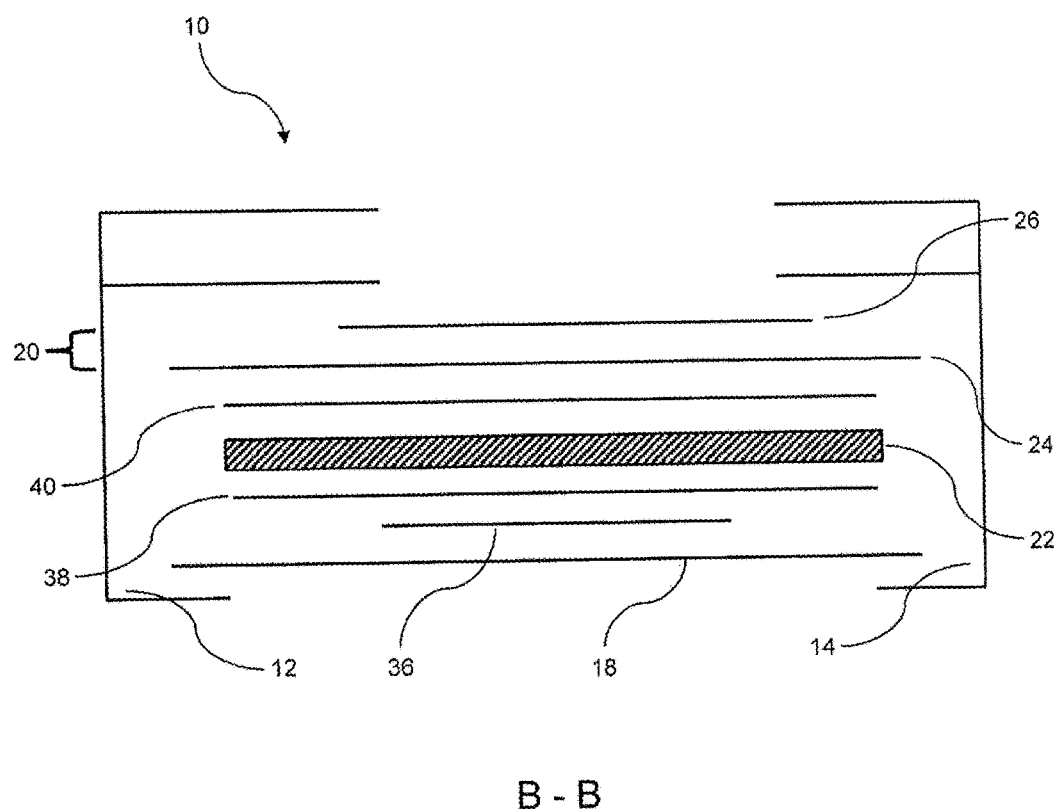
FIG. 3 shows a schematic exploded cross-sectional view taken along the line B-B in FIG. 1.

The absorbent article 10 includes a front panel 12, a back panel 14 and a crotch panel 16 bridging and partially overlapping the front panel 12 and the back panel 14. The crotch panel 16 includes a liquid permeable topsheet 18 (see FIGS. 2 and 3), a liquid impermeable backsheet 20, and an absorbent core 22 provided between the topsheet 18 and the backsheet 20, as is schematically shown in FIGS. 2 and 3. The absorbent core 22 is indicated by a rectangle drawn with a dashed line in FIG. 1.

The backsheet 20 has a laminate structure including a liquid barrier sheet 24 and a nonwoven layer 26 arranged on top of each other (see FIGS. 2 and 3). The nonwoven layer 26 is arranged at an outer side of the crotch panel 16 (i.e., the upper side in FIGS. 2 and 3), facing away from a wearer of the absorbent article 10 when worn. The liquid barrier sheet 24 may be, for example, made of a plastic material, e.g., a thermoplastic film material. In particular, the liquid barrier sheet 24 may be a breathable microporous film comprising a thermoplastic elastomeric polyolefin polymer and a filler.

The liquid barrier sheet 24 extends over the entire length, in the direction from the front panel 12 towards the back panel 14, of the crotch panel 16. The nonwoven layer 26 extends over the entire length, in the direction from the front panel 12 towards the back panel 14, of the portion of the crotch panel 16 arranged between the front panel 12 and the back panel 14. Further, the nonwoven layer 26 partially overlaps with the front panel 12 and the back panel 14, as is shown in FIG. 1. Specifically, the nonwoven layer 26 extends over the front panel 12 over a length, in the direction from the front panel 12 towards the back panel 14, in the range of 5 mm to 40 mm, and the nonwoven layer 26 extends over the back panel 14 over a length, in the direction from the front panel 12 towards the back panel 14, in the range of 5 mm to 40 mm.

The length, in the direction from the front panel 12 towards the back panel 14, of the nonwoven layer 26 is in the range of 50% to 60% of the length, in the direction from the front panel 12 towards the back panel 14, of the liquid barrier sheet 24. As is shown in FIG. 1, the width, in the direction perpendicular to the direction from the front panel 12 towards the back panel 14, of the nonwoven layer 26 is smaller than the width, in the direction perpendicular to the direction from the front panel 12 towards the back panel 14, of the liquid barrier sheet 24.

The crotch panel 16 further includes a nonwoven cuff material 28. As is shown in FIG. 2, the nonwoven cuff material 28 consists of two separate pieces of material, i.e., two separate nonwoven layers, wrapped around side edges of the remainder of the crotch panel 16. Inner edges 30 of the nonwoven cuff material 28 at the outer side of the crotch panel 16 (the upper side in FIG. 2) extend along the direction from the front panel 12 towards the back panel 14, as is shown in FIG. 1 where the inner edges 30 of the nonwoven cuff material 28 are indicated by dashed lines.

The inner edges 30 of the nonwoven cuff material 28 are spaced apart from each other by a distance in the direction perpendicular to the direction from the front panel 12 towards the back panel 14 (see FIGS. 1 and 2). The width, in the direction perpendicular to the direction from the front panel 12 towards the back panel 14, of the nonwoven layer 26 is larger than the distance between the inner edges 30 of the nonwoven cuff material 28, so that the nonwoven layer 26 extends beyond each of the inner edges 30 of the nonwoven cuff material 28 in the direction perpendicular to the direction from the front panel 12 towards the back panel 14. In particular embodiments, the nonwoven layer 26 extends beyond each of the inner edges 30 of the nonwoven cuff material 28 in the direction perpendicular to the direction from the front panel 12 towards the back panel 14 by 1 mm to 25 mm.

As is shown in FIG. 1, the front panel 12, the back panel 14, the crotch panel 16, the liquid barrier sheet 24 and the nonwoven layer 26 each have a rectangular shape in plan view in the fully unfolded and laid out flat state. Thus, these components can be manufactured in a particularly simple manner, substantially without any material losses.

The liquid barrier sheet 24 has printed areas (not shown) at the portion 32 thereof which overlaps with the front panel 12 and the portion 34 thereof which overlaps with the back panel 14 (see FIG. 1). The nonwoven layer 26 does not extend into these printed areas, as is indicated in FIG. 1. Therefore, clear and sharp prints with good visibility are provided in these printed areas.

The nonwoven layer 26 is arranged relative to the liquid barrier sheet 24 so that a center line of the nonwoven layer 26 along the direction from the front panel 12 towards the back panel 14 is substantially congruent with a center line of the liquid barrier sheet 24 along the direction from the front panel 12 towards the back panel 14 (see FIG. 1).

Further, the nonwoven layer 26 is arranged relative to the liquid barrier sheet 24 so that a center line of the nonwoven layer 26 along the direction perpendicular to the direction from the front panel 12 towards the back panel 14 is substantially congruent with a center line of the liquid barrier sheet 24 along the direction perpendicular to the direction from the front panel 12 towards the back panel 14 (see FIG. 1).

The crotch panel 16 further includes an optional transfer layer 36 provided between the topsheet 18 and the absorbent core 22 (see FIGS. 2 and 3) for ensuring efficient transfer and distribution of liquids, such as urine or other bodily fluids, from the topsheet 18 to the absorbent core 22. The transfer layer 36 may be a 40 to 90 gsm thermoplastic nonwoven material, such as of PET, PE, PP.

The absorbent article 10 can further include an optional tissue or nonwoven layer 38 arranged between the transfer layer 36 and the absorbent core 22, and an optional core cover layer 40 arranged between the absorbent core 22 and the liquid barrier sheet 24, as is shown in FIG. 3. The tissue layer and the nonwoven layer may be of 6 to 20 gsm. The tissue layer may be a cellulose-based material and the nonwoven layer may be a thermoplastic material, such as of PET, PE, PP.

The different components of the absorbent article 10, i.e., the topsheet 18, the backsheet 20, the absorbent core 22, the liquid barrier sheet 24 and the nonwoven layer 26, may have the configurations and be made of the materials described in detail above.

The different components of the absorbent article 10 may be attached to each other, for example, by thermo-mechanical bonding, such as thermosealing, ultrasonic bonding, such as ultrasonic welding, an adhesive or adhesives, stitching or the like. In particular, the liquid barrier sheet 24 and the nonwoven layer 26 may be attached to each other by thermosealing and/or by ultrasonic welding and/or by an adhesive or adhesives.

The wearable disposable absorbent article 10 as shown in FIGS. 1 to 3 offers a large printable area, in particular, in the portions 32 and 34 of the liquid barrier sheet 24 which overlap with the front panel 12 and the back panel 14, respectively. This printable area allows for clear and sharp prints with good visibility to be provided. Further, the absorbent article 10 can be manufactured in a cost-efficient manner, substantially without any cutting losses.

Moreover, in the embodiment of FIGS. 1 to 3, the width, in the direction perpendicular to the direction from the front panel 12 towards the back panel 14, of the nonwoven layer 26 is smaller than the width, in the direction perpendicular to the direction from the front panel 12 towards the back panel 14, of the liquid barrier sheet 24. By providing, in this manner, a smaller amount of nonwoven material of the nonwoven layer 26 in the width direction of the nonwoven layer 26 and the liquid barrier sheet 24, a particularly soft and pliable absorbent article 10 with a high degree of leakage protection can be obtained.

All of the above are fully within the scope of the present invention, and are considered to form the basis for alternative embodiments in which one or more combinations of the above-described features are applied, without limitation to the specific combinations disclosed above.

In light of this, there will be many alternatives which implement the teaching of the present invention. It is expected that one skilled in the art will be able to modify and adapt the above disclosure to suit his own circumstances and requirements within the scope of the present invention, while retaining some or all technical effects of the same, either disclosed or derivable from the above, in light of his common general knowledge in this art. All such equivalents, modifications or adaptations fall within the scope of the invention hereby defined and claimed.

The invention claimed is:

1. A wearable disposable absorbent article comprising:
   a front panel;
   a back panel; and
   a crotch panel bridging and at least partially overlapping the front panel and the back panel; wherein
   the crotch panel comprises:
      a topsheet;
      a backsheet having a laminate structure comprising a liquid barrier sheet and a nonwoven layer arranged on top of each other; and
      an absorbent core provided between the topsheet and the backsheet,
   wherein the nonwoven layer is arranged at an outer side of the crotch panel, facing away from a wearer of the absorbent article when worn,
   wherein the liquid barrier sheet extends over the entire length, in the direction from the front panel towards the back panel, of the portion of the crotch panel arranged between the front panel and the back panel, and the liquid barrier sheet further extends over at least a portion of the front panel and over at least a portion of the back panel,
   wherein the nonwoven layer extends at least over the entire length, in the direction from the front panel towards the back panel, of the portion of the crotch panel arranged between the front panel and the back panel,
   wherein the nonwoven layer does not extend over the front panel over a length, in the direction from the front panel towards the back panel, of more than 40 mm,
   wherein the nonwoven layer does not extend over the back panel over a length, in the direction from the front panel towards the back panel, of more than 40 mm, and
   wherein the width, in the direction perpendicular to the direction from the front panel towards the back panel, of the nonwoven layer is smaller than the width, in the direction perpendicular to the direction from the front panel towards the back panel, of the liquid barrier sheet, wherein the relative dimensions given for the absorbent article relate to the fully unfolded and laid out flat state of the absorbent article.

2. The wearable disposable absorbent article according to claim 1, wherein the liquid barrier sheet is made of a plastic material and/or a nonwoven material.

3. The wearable disposable absorbent article according to claim 1, wherein the liquid barrier sheet extends over the entire length, in the direction from the front panel towards the back panel, of the crotch panel.

4. The wearable disposable absorbent article according to claim 1, wherein the nonwoven layer extends over the front panel over a length, in the direction from the front panel towards the back panel, in the range of 5 mm to 40 mm and/or the nonwoven layer extends over the back panel over a length, in the direction from the front panel towards the back panel, in the range of 5 mm to 40 mm.

5. The wearable disposable absorbent article according to claim 1, wherein the length, in the direction from the front panel towards the back panel, of the nonwoven layer is in the range of 40% to 70% of the length, in the direction from the front panel towards the back panel, of the liquid barrier sheet.

6. The wearable disposable absorbent article according to claim 1, wherein the width, in the direction perpendicular to the direction from the front panel towards the back panel, of the nonwoven layer is smaller than the width, in the direction perpendicular to the direction from the front panel towards the back panel, of the liquid barrier sheet by not more than 50 mm.

7. The wearable disposable absorbent article according to claim 1, wherein the crotch panel further comprises a nonwoven cuff material having inner edges at the outer side of the crotch extending along the direction from the front panel towards the back panel,
wherein the inner edges of the nonwoven cuff material are spaced apart from each other by a distance in the direction perpendicular to the direction from the front panel towards the back panel, and
wherein the width, in the direction perpendicular to the direction from the front panel towards the back panel, of the nonwoven layer is larger than the distance between the inner edges of the nonwoven cuff material, so that the nonwoven layer extends beyond each of the inner edges of the nonwoven cuff material in the direction perpendicular to the direction from the front panel towards the back panel.

8. The wearable disposable absorbent article according to claim 7, wherein the nonwoven layer extends beyond each of the inner edges of the nonwoven cuff material in the direction perpendicular to the direction from the front panel towards the back panel by 30 mm or less.

9. The wearable disposable absorbent article according to claim 1, wherein at least one of the front panel, the back panel, the crotch panel, the nonwoven layer, and the liquid barrier sheet has a substantially rectangular shape in plain view.

10. The wearable disposable absorbent article according to claim 1, wherein the absorbent article has an H-shape in plain view.

11. The wearable disposable absorbent article according to claim 1, wherein the liquid barrier sheet has one or more printed areas at the portion thereof which overlaps with the front panel and/or the portion thereof which overlaps with the back panel, and
the nonwoven layer does not extend into the one or more printed areas.

12. The wearable disposable absorbent article according to claim 1, wherein the liquid barrier sheet and the nonwoven layer are attached to each other by thermosealing, by ultrasonic welding, or by an adhesive.

13. The wearable disposable absorbent article according to claim 1, wherein the liquid barrier sheet is a breathable layer or a non-breathable layer.

14. The wearable disposable absorbent article according to claim 1, wherein the liquid barrier sheet has a basis weight in the range of 8 $g/m^2$ to 22 $g/m^2$.

15. The wearable disposable absorbent article according to claim 1, wherein the absorbent article is a diaper, an incontinence garment, or a feminine garment.

16. The wearable disposable absorbent article according to claim 1, wherein the nonwoven layer consists of a single piece of nonwoven material.

* * * * *